United States Patent

Simmons, Jr.

[11] Patent Number: 6,102,930
[45] Date of Patent: Aug. 15, 2000

[54] VOLUMETRIC MEASUREMENT DEVICE AND METHOD IN LATERAL RECESS AND FORAMINAL SPINAL STENOSIS

[76] Inventor: Edward D. Simmons, Jr., 59 S. Woodside La., Williamsville, N.Y. 14221

[21] Appl. No.: 09/079,847

[22] Filed: May 15, 1998

Related U.S. Application Data

[60] Provisional application No. 60/046,707, May 16, 1997.

[51] Int. Cl.[7] .................................................. A61M 29/00
[52] U.S. Cl. ............................................. 606/194; 604/97
[58] Field of Search .................................... 606/194, 106, 606/99–105, 61–69; 623/17, 18, 19; 604/97, 100

[56] References Cited

U.S. PATENT DOCUMENTS

| | | | |
|---|---|---|---|
| 5,013,318 | 5/1991 | Spranza, III | 606/102 |
| 5,239,982 | 8/1993 | Trauthen | 128/4 |
| 5,383,855 | 1/1995 | Nicholson et al. | 604/100 |
| 5,562,736 | 10/1996 | Ray et al. | 632/17 |

*Primary Examiner*—Michael Buiz
*Assistant Examiner*—Lien Ngo
*Attorney, Agent, or Firm*—Hodgson, Russ, Andrews, Woods & Goodyear LLP

[57] ABSTRACT

A device for accurately determining the lateral recess and foraminal volume prior to and following spinal decompression procedures to assess adequacy of the decompression. The device comprises an inflatable tipped catheter connected to calibration instruments that will correspondingly give volume of inflation of the tip of the catheter which is placed in the lateral recess or nerve root foramen. The readings can be used to determine the extent of the decompression and objectively quantify the extent of such decompression.

10 Claims, 2 Drawing Sheets

VOLUMETRIC MEASUREMENT DEVICE AND METHOD IN LATERAL RECESS AND FORAMINAL SPINAL STENOSIS

CROSS REFERENCE TO A RELATED APPLICATION

Applicant hereby claims priority based on Provisional Application Ser. No. 60/046,707 filed May 16, 1997 and entitled "Volumetric Measurement Device And Method In Lateral Recess And Foraminal Spinal Stenosis" which is incorporated herein by reference.

BACKGROUND OF THE INVENTION

This invention relates generally to the art of medical diagnostic instruments and methods of using the same, and more particularly to a new and improved device and method for more accurately determining the lateral recess and foraminal volume prior to and following spinal decompression procedures.

In degenerative conditions of the spine narrowing of the nerve root, narrowing of the lateral recess and foramen, with nerve root compression, can occur due to loss of disc space height, subluxation, facet joint hypertrophy, osteophyte formation, and ligamentum flavum hypertrophy along with other causes. The ultimate loss in volume through the lateral recess and foramen results in compression of the nerve root structures. This gives rise to symptoms of radicular pain and dysfunction in the lower extremities. Surgical treatment for this involves decompression and removal of bony and soft tissue elements that are compressing the nerve in the lateral recess and foramen. Presently probes are commonly used to assess adequacy of decompression.

SUMMARY OF THE INVENTION

The present invention provides a device that can more accurately determine the lateral recess and foraminal volume prior to and following decompression to assess the degree of compression and the adequacy of the decompression. The device of the present invention comprises an inflatable tipped catheter connected to calibration instruments that will correspondingly give volume of inflation of the tip of the catheter which is placed in the lateral recess or nerve root foramen. The readings can be used to determine the extent of the decompression and more objectively quantify the extent of such decompression.

The following detailed description of the invention, when read in conjunction with the accompanying drawings wherein the same reference numerals denote the same or similar parts throughout the several views, is in such full, clear, concise and exact terms as to enable any person skilled in the art to which it pertains, or with which it is mostly nearly connected, to make and use the invention.

DETAILED DESCRIPTION OF THE ILLUSTRATED EMBODIMENT

Figure 1:
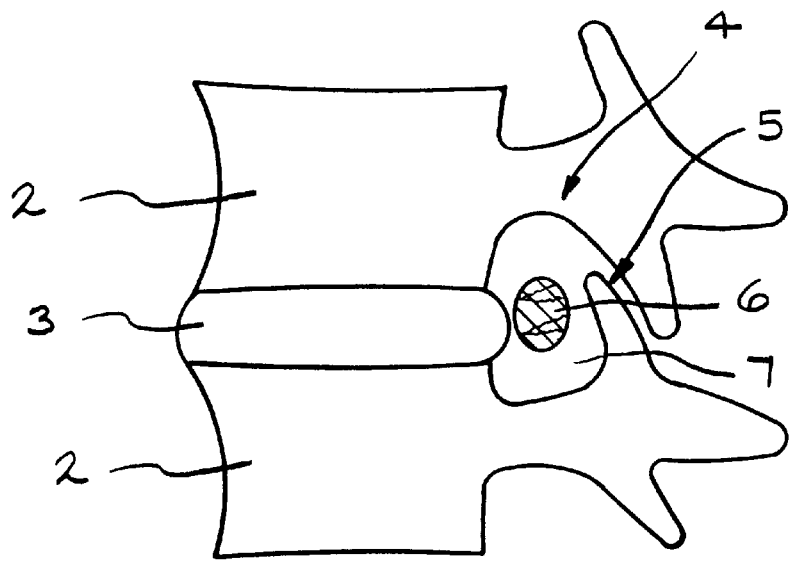
FIG. 1 is a sagittal view at level of foramen and illustrating a normal spinal situation.

FIG. 1 is a sagittal view at level of foramen of the spine including vertebral body 2, disc 3, pedicle 4, facet joint 5 and nerve root in foramen 6. This is a normal situation wherein ample room and free space 7 is around the nerve root 6.

Figure 2:
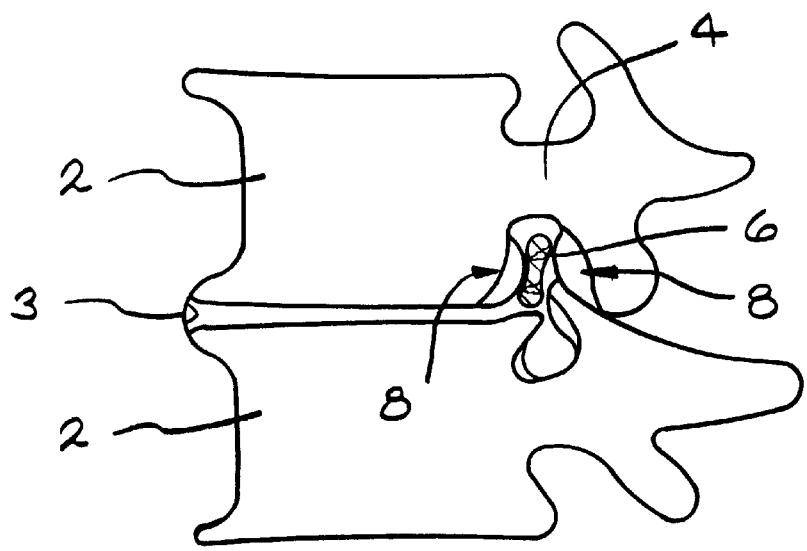
FIG. 2 is a sagittal view at level of foramen and illustrating an abnormal situation with lateral recess and foraminal spinal stenosis.

FIG. 2 is a sagittal view at level of foramen illustrating an abnormal situation with lateral recess and foraminal spinal stenosis. In this situation there is collapse of disc space and bone osteophytes with facet hypertrophy (enlargement) causing severe compression of nerve root 6. The shaded areas 8 represent bone overgrowth in the nerve root foramen.

Figure 3:
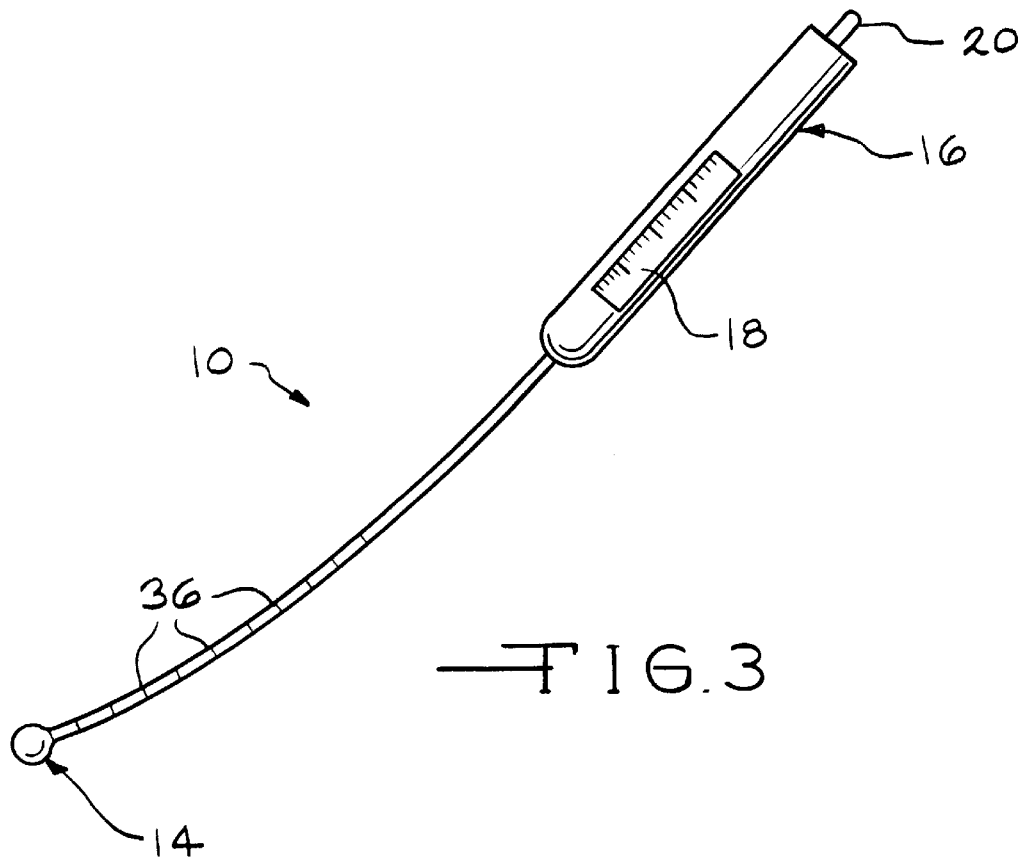
FIG. 3 is a perspective view of the flexible spinal catheter device according to the present invention.

The device 10 of the present invention is shown in FIG. 3 and comprises a flexible catheter 12 of appropriate length for the procedure to be described herein and having an inflatable tip 14 on the end thereof. The opposite end of catheter 12 is connected to a housing 16 provided with a readout device 18 for indicating the volume of inflation of tip 14. Housing 16 is provided with a fitting 20 for connection to a source (not shown) of fluid, i.e. gas or liquid, for supplying pressure to inflate and deflate tip 14 in a controlled manner. Tip 14 when inflated is generally spherical in shape.

Figure 4:
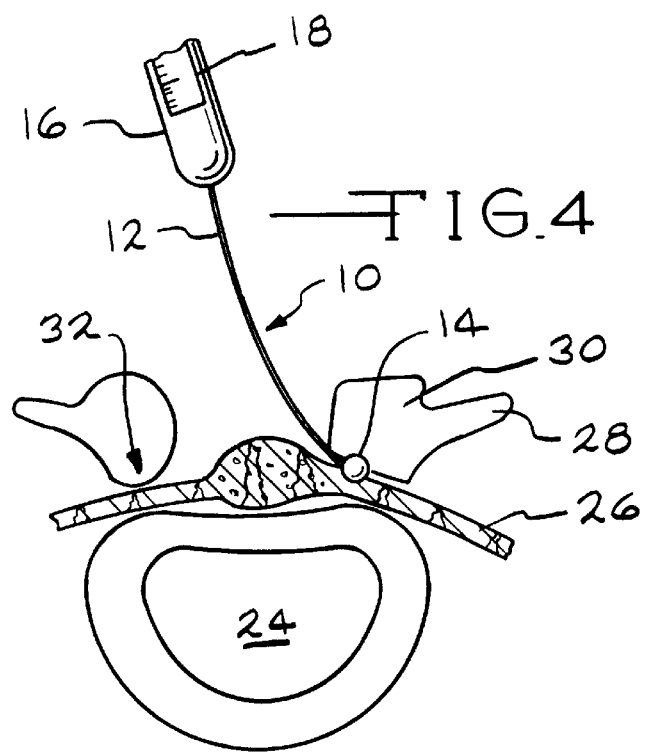
FIG. 4 is a fragmentary sectional view showing the flexible spinal catheter device of FIG. 3 during use when inserted into the lateral recess area of the spine.

The manner in which the flexible spinal catheter device 10 of the present invention is used is illustrated in FIG. 4 which includes a fragmentary sectional view of a patient's spine indicating the relative locations of disc 24, nerve root 26, transverse process 28, facet joint 30 and lateral recess and foramen 32.

The patient is under general anesthesia and is placed prone on a standard spinal operating table. The back is prepped and draped. A standard midline posterior incision is made. A laminectomy or laminotomy is performed at the appropriate vertebral segment to allow for access to the spinal canal. Following removal of a portion or all of the lamina, the lateral recess and/or foramen can be probed to assess for patency and volume measurement. (The dural sac and nerve root can be seen and the path of the nerve root through the lateral recess can be seen and probed. The facet joint forms a border and "roof" over the lateral recess area. The nerve root then passes out through the foramen, passing underneath the pedicle and laterally through the foramen.) To conduct the probing and measurement procedure, the balloon end 14 of the flexible catheter tip is inserted into the lateral recess and/or foramen and is inflated to a predetermined measurement pressure as shown in FIG. 4. To achieve this, the tip of the catheter 14 is grasped and maneuvered manually into the lateral recess and foraminal area. It is slowly advanced alongside the nerve root to a point where it enters an area of compression. The depth of the insertion of the catheter 12 is noted by observing the relative position of markers 36 on the catheter 12 vis-a-vis bony adjacent landmarks. At this point, the catheter tip 14 is inflated and the volume of the tip inflation is recorded. This gives an indication of the volume of the lateral recess and/or foramen. The catheter tip 14 then is deflated and the catheter 12 is removed.

One way to ascertain the predetermined measurement pressure is a manual or tactile approach. During initial inflation of balloon end 14 while in the area of compression no detectable resistance to the inflation is sensed or felt by the fingers of the surgeon manipulating the device. As inflation of end 14 continues a point will be reached where the surgeon begins to sense or feel some resistance to the inflation by the area of compression. The predetermined pressure is that level of inflation pressure where a reasonable amount of resistance to further inflation is detected.

Decompression of the lateral recess and foramen is now carried out in standard fashion (with removal of a portion of the facet joint). Re-measurement of the volume in the (now decompressed) lateral recess and/or foramen is again carried out by re-inserting the balloon end 14 of the catheter, noting the previously recorded depth of insertion of catheter 12, and re-inflating the end to the predetermined measurement pressure as previously described and as shown in FIG. 4. The measured volume is recorded and can be compared to the "pre-decompression" volume.

The foregoing method utilizing the device 10 of the present invention provides an accurate determination of the lateral recess and foraminal volume prior to and following decompression to assess adequacy of the decompression. The compared measured volume readings are used to determine the extent of the decompression and provide an objective quantification of the same.

By way of example, in an illustrative device 10 according to the present invention, inflatable tip 14 can be of latex type material which is stretchable and medical grade, i.e. human body reaction-free. Typically the diameter of tip 14 is about 1.5 mm when deflated and a maximum of about 8.0 mm–1.0 cm when inflated. The lumen or catheter portion 12 of device 10 is of any suitable flexible and medical grade plastic material and has an inner diameter of about 0.5 mm and an outer diameter of about 1.5 mm.

A device according to the present invention, with inflatable tip and volume measuring, has been used as described in four cases. The diagnosis of each of the four patients was spinal stenosis, particularly involving the lateral recess and foraminal areas. Measurement of lateral recess and foraminal volume was carried out using the device of the present invention prior to the decompression and again afterward. In this way, the amount of decompression of the nerve root could be quantified in each case. (The unit of volume measurement is 0.1 cc). There were no difficulties encountered in any of the four cases and the measurement procedure took under two minutes in each case. The device used is similar to that shown in FIG. 1. The actual length of that device is about 9" long. The catheter is approximately 1.5 mm in diameter. The balloon tip can be inflated to approximately 1.0 cm in diameter.

It is therefore apparent that the present invention accomplishes its intended objects. While an embodiment of the present invention has been described in detail, that is for purposes of illustration, not limitation.

What is claimed is:

1. A device for determining lateral recess and foraminal volume prior to and following spinal decompression procedures comprising:
   a) a flexible catheter having first and second ends;
   b) an inflatable tip at said first end of said catheter, said tip when deflated being of a size such that it can be inserted into the lateral recess and/or foramen of the spine by manipulation of said catheter, said tip being inflatable to a size indicating the volume of the lateral recess and/or foramen into which it is inserted by enabling manual sensing through said catheter of resistance to further inflation of said tip by an area of compression where said tip is inserted;
   c) means at said second end of said catheter for connection to a source of fluid under pressure for inflating said tip; and
   d) readout means operatively associated with said catheter for indicating the volume of inflation of said tip;
   e) so that said tip can be inserted and inflated in the lateral recess and/or foramen and the volume indicated by said readout means recorded prior to and after a spinal decompression procedure to assess the adequacy of the decompression procedure by comparing recorded volumes of inflation of said tip obtained from said readout means.

2. A device according to claim 1, further including visible markings on said catheter to indicate depth of insertion into the lateral recess and or foramen.

3. A device according to claim 1, wherein said tip is of stretchable medical grade material.

4. A device according to claim 1, wherein said tip has a diameter in a range from about 1.5 mm when deflated to about 1.0 cm when inflated.

5. A device according to claim 1, wherein said catheter has a length of no greater than about one foot.

6. A device according to claim 1, wherein said tip is generally in the shape of a sphere.

7. A method for determining lateral recess and foraminal volume prior to and following spinal decompression procedures comprising:
   a) providing a catheter having an inflatable tip at one end and connected at the other end to a source of fluid under pressure and having means for indicating the volume of inflation of the catheter tip;
   b) inserting the catheter tip while deflated into the lateral recess and/or foramen of a patient prior to a spinal decompression procedure;
   c) inflating the catheter tip and obtaining a first indication of volume of tip inflation;
   d) deflating the catheter tip and removing the tip from the lateral recess and/or foramen;
   e) re-inserting the catheter tip while deflated into the lateral recess and/or foramen of the patient following a spinal decompression procedure;
   f) inflating the catheter tip and obtaining a second indication of volume of tip inflation; and
   g) utilizing the indications of volume of tip inflation to assess the adequacy of the spinal decompression procedure.

8. A method according to claim 7, wherein said step of utilizing the volume indications includes comparing the first and second indications of volume of tip inflation.

9. A method according to claim 7, further including observing the depth of insertion of the catheter into the lateral recess and/or foramen prior to obtaining the first indication of volume of tip inflation and utilizing the observed depth of insertion during said step of re-inserting the catheter.

10. A method according to claim 7, wherein the catheter tip is inflated to substantially the shape of a sphere having a maximum diameter of about 1.0 cm.

* * * * *